United States Patent [19]
Tom et al.

[11] Patent Number: 5,817,921
[45] Date of Patent: Oct. 6, 1998

[54] PIEZOELECTRIC ENVIROMENTAL FLUID MONITORING ASSEMBLY AND METHOD

[75] Inventors: Glenn M. Tom, New Milford; Cynthia A. Miller, Bethel, both of Conn.

[73] Assignee: Advanced Technology Materials, Inc., Danbury, Conn.

[21] Appl. No.: 679,258

[22] Filed: Jul. 12, 1996

[51] Int. Cl.$^6$ ................................................. G01N 29/02
[52] U.S. Cl. ........................................ 73/24.01; 73/24.06
[58] Field of Search ................................. 73/23.31, 24.01, 73/24.04, 24.06

[56] References Cited

U.S. PATENT DOCUMENTS

| | | | |
|---|---|---|---|
| 3,744,296 | 7/1973 | Beltzer | 73/24.01 X |
| 4,446,720 | 5/1984 | Sinclair | 73/24.06 |
| 5,042,288 | 8/1991 | Vig | 73/24.01 |
| 5,065,140 | 11/1991 | Neuburger | 73/24.04 X |
| 5,138,869 | 8/1992 | Tom . | |
| 5,151,395 | 9/1992 | Tom . | |
| 5,208,162 | 5/1993 | Osborne et al. | 73/24.01 X |
| 5,339,675 | 8/1994 | DiLeo et al. | 73/24.06 X |

FOREIGN PATENT DOCUMENTS 06-308008  11/1994  Japan ..................... 73/24.01

OTHER PUBLICATIONS

Neuburger, Glen G., "Detection of Ambient Hydrogen Chloride with a Zinc–Coated Piezoelectric Crystal Resonator Operating in a Frequency–Time Different Mode," Anal. Chem. 1989, 61, 1559–1563.

Levenson, Leonard L., "II. Chemisorption on Single Element Thin Films," in *Applications of Piezoelectric Quartz Crystal Microbalances*, C. Lu, editor, vol. 7, Elsevier, Amsterdam, 1984, pp. 198–203.

*Primary Examiner*—Hezron E. Williams
*Assistant Examiner*—Daniel S. Larkin
*Attorney, Agent, or Firm*—Steven J. Hultquist; Oliver A. M. Zitzmann

[57] ABSTRACT

An environmental gas monitor for detection of a trace fluid component in a fluid environment, comprising: a piezoelectric crystal having a fundamental resonant frequency in response to an applied oscillating electric field; a coating on the piezoelectric crystal of a sensor material which is reactive with the trace fluid component to yield a solid interaction product; means for applying an oscillating electric field to the piezoelectric crystal which generates an output resonant frequency therefrom; means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment; means, e.g., an eductor, for flowing fluid from the fluid environment at a constant flow rate to the coating on the piezoelectric crystal so that the trace fluid component when present reacts with the coating to form the solid interaction product; wherein the coated piezoelectric crystal exhibits a frequency response rate to the trace fluid component in the range of from about 0.001 to about 1000 Hertz/min/(part-per-million of the fluid component).

18 Claims, 7 Drawing Sheets

PIEZOELECTRIC ENVIROMENTAL FLUID MONITORING ASSEMBLY AND METHOD

BACKGROUND OF THE INVENTION

1. Field of the Invention

The present invention relates to a sensor for detection and monitoring of low/trace concentration fluid components, to a fluid processing apparatus and method utilizing same. The sensor apparatus and method of the invention have utility, inter alia, as an environmental monitor for detection of hazardous and other undesirable components in fluid environments such as ambient air.

2. Description of the Related Art

In the field of environmental gas monitoring, various means have been employed and/or proposed for the detection of low or trace concentrations of impurities, e.g., hazardous gas species, in air or other ambient gases. The systems currently commercially available such as the so-called MDA monitors or Kitagawa tubes, are either costly, require significant maintenance (involving replacement of consumable elements, e.g., the frequent change of color tapes in MDA monitors), require frequent recalibration, and in some instances do not measure the impurity species properly or provide useful readouts. The MDA monitor is sensitive only down to concentration levels on the order of about 5 ppm, and readings below that level are inaccurate.

In general, problems of cost, accuracy, and reliability plague the existing commercially available environmental gas monitors.

Accordingly, it would be a significant advance in the art to provide a low cost, accurate, reliable, and easily fabricated and operated sensor device for monitoring of impurity species in fluid environments, such as ambient gas environments which are monitored for the presence of contaminants.

It is another object of the invention to provide a highly sensitive and selective detection system for determining the presence of impurity species in fluid environments.

Other objects and advantages of the invention will be more fully apparent from the ensuing disclosure and appended claims.

SUMMARY OF THE INVENTION

The present invention relates to an environmental gas monitor for detection of a trace fluid component in a fluid environment, comprising:

a piezoelectric crystal having a fundamental resonant frequency in response to an applied oscillating electric field;

a coating on the piezoelectric crystal of a sensor material which is reactive with the trace fluid component to yield a solid interaction product of changed mass in relation to initial mass of the sensor material interacting with the trace fluid component to yield the solid interaction product;

means for applying an oscillating electric field to the piezoelectric crystal which generates an output resonant frequency therefrom;

means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment; and means for flowing fluid from the fluid environment at a constant flow rate to the coating on the piezoelectric crystal so that the trace fluid component when present reacts with the coating to form the solid interaction product;

wherein the coated piezoelectric crystal exhibits a frequency response rate to the trace fluid component in the range of from about 0.001 to about 1000 Hertz/min/(part-per-million of the fluid component).

In a specific aspect of such environmental gas monitor, the presence of water vapor in the environment is concurrently sensed by a second, preferably hygrometric, sensor, and the determined water vapor (relative humidity) concentration is utilized to correct or adjust the concentration determined for the trace fluid component to take into account any water vapor which would otherwise alter the concentration determination of the trace fluid component.

Preferably, the coated piezoelectric crystal exhibits a frequency response rate to the trace fluid component in the range of from about 0.01 to about 100 Hertz/min/(part-per-million of the fluid component); more preferably, such range is from about 0.1 to about 50 Hertz/min/(part-per-million of the fluid component); and most preferably such range is from about 0.5 to about 10 Hertz/min/(part-per-million of the fluid component).

The means for flowing fluid from the fluid environment to the coating on the piezoelectric crystal may for example comprise an eductor having appropriate geometry, e.g., length and diameter characteristics, and/or containing a flow limiting structure such as a frit or flow-restricting orifice, so that the flow of fluid to the coating is maintained at a constant rate, with the pressure on the low pressure side of the flow restriction being less than ½ the pressure on the upstream side of the flow restriction.

In such sensor, the piezoelectric crystal may for example comprise a piezoelectric silica crystal. The coating of sensor material used in practicing the invention may comprise a chemisorbent material which is chemically reactive with the trace fluid component. Useful piezoelectric crystals include those having a fundamental resonant frequency in the range of from about 1 megahertz to about 10 megahertz.

In the sensor of the invention, the means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment, may comprise means such as a circuit including therein a cascaded array of frequency counters.

The sensor may be constructed and arranged so that the output indicative of the presence of the trace fluid component in the environment, comprises a calculated concentration of said trace fluid component in said environment.

In one embodiment of the invention, the sensor further comprises a flow control means for controllably flowing a selected flow rate of fluid from the fluid environment into contact with the sensor material on the piezoelectric crystal, and the aforementioned means for performing functions (i), (ii) and (iii), comprise computational means for determining the calculated concentration of the trace fluid component in the fluid environment, in accordance with the algorithm:

$$dF/dt = \delta[C_i]Q$$

wherein:

dF/dt is the time-variant differential rate of change of frequency from the fundamental resonant frequency of the piezoelectric crystal coated with the sensor material as sampled by the means for performing functions (i), (ii) and (iii);

δ is a proportionality constant;

$[C_i]$ is the concentration of the trace fluid component; and

Q is the volumetric flow rate of the fluid of the fluid environment.

The sensor in another embodiment further comprises a flow passage accommodating flow therethrough of fluid from the fluid environment, and having a flow restrictor in the passage, arranged in relation to the sensor material to restrict flow of fluid from the environment to the sensor material. Such diffusional flow restrictor additionally is constructed and arranged to prevent particulate solids in the fluid environment from contacting the sensor material.

The sensor material in one aspect may comprise a thin film metal, such as copper, zinc, silver, aluminum, chromium, or the like.

A further aspect of the invention relates to a process for monitoring a fluid stream for determining presence of a selected component therein, such process comprising:

providing a sensor for detection of the selected component in the fluid stream, such sensor comprising:

(A) a piezoelectric crystal having a fundamental resonant frequency in response to an applied oscillating electric field;

(B) a coating on the piezoelectric crystal of a sensor material which is reactive with the selected component to yield a solid interaction product of changed mass in relation to initial mass of the sensor material interacting with the selected component to yield the solid interaction product;

applying an oscillating electric field to the piezoelectric crystal which generates an output resonant frequency therefrom;

sampling the output resonant frequency of the piezoelectric crystal while the oscillating electric field is applied thereto;

flowing fluid from the fluid environment at a constant flow rate to the coated piezoelectric crystal, and determining the change in resonant frequency from the fundamental resonant frequency upon formation of the solid interaction product when the sensor material interacts with the selected component in the fluid stream; and generating an output indicative of the presence of the selected component in the fluid stream.

In such process, the step of generating the output indicative of the presence of the selected component in the fluid stream, comprises determining via a programmed computer a calculated concentration of the selected component in the fluid stream.

The process may further comprise controllably flowing at least a portion of the fluid stream at a selected flow rate in contact with the sensor material on the piezoelectric crystal, and determining the calculated concentration of the selected component in the fluid stream, in accordance with the algorithm:

$$dF/dt = \delta[C_i]Q$$

wherein:

dF/dt is the time-variant differential rate of change of frequency from the fundamental resonant frequency of the piezoelectric crystal coated with the sensor material as sampled;

δ is a proportionality constant;

$[C_i]$ is the concentration of the selected component in the fluid stream; and

Q is the volumetric flow rate of the fluid stream.

Such determination of the concentration of the selected component may be accompanied by the sensing and determination of the concentration of water vapor content in the environment, with adjustment or correction of the concentration of the selected component to compensate for such presence of water vapor. The water vapor sensing may be effected by hygrometric sensing of the water vapor, and such hygrometric sensing may likewise be based on a piezoelectric sensor comprising a coating interactive with water vapor.

In the process of the invention, the selected component may for example comprise a halide gas. By way of further example, the selected component may comprise a gas such as boron trichloride, boron trifluoride, hydrogen chloride, chlorine, fluorine, hydrogen fluoride, etc.

In another aspect, the environmental fluid monitor of the invention comprises a coated piezoelectric crystal, whose coating is reactive with the trace fluid component, and which is arranged in the sensor apparatus in relation to the fluid flow stream from the fluid environment so that the coated piezoelectric crystal exhibits a frequency response rate to the trace fluid component in the range of from about 0.001 to about 1000 Hertz/min/(part-per-million of the fluid component), preferably in the range of from about 0.01 to about 100 Hertz/min/(part-per-million of the fluid component), more preferably in the range of from about 0.1 to about 50 Hertz/min/(part-per-million of the fluid component), and most preferably in the range of from about 0.5 to about 10 Hertz/min/(part-per-million of the fluid component).

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
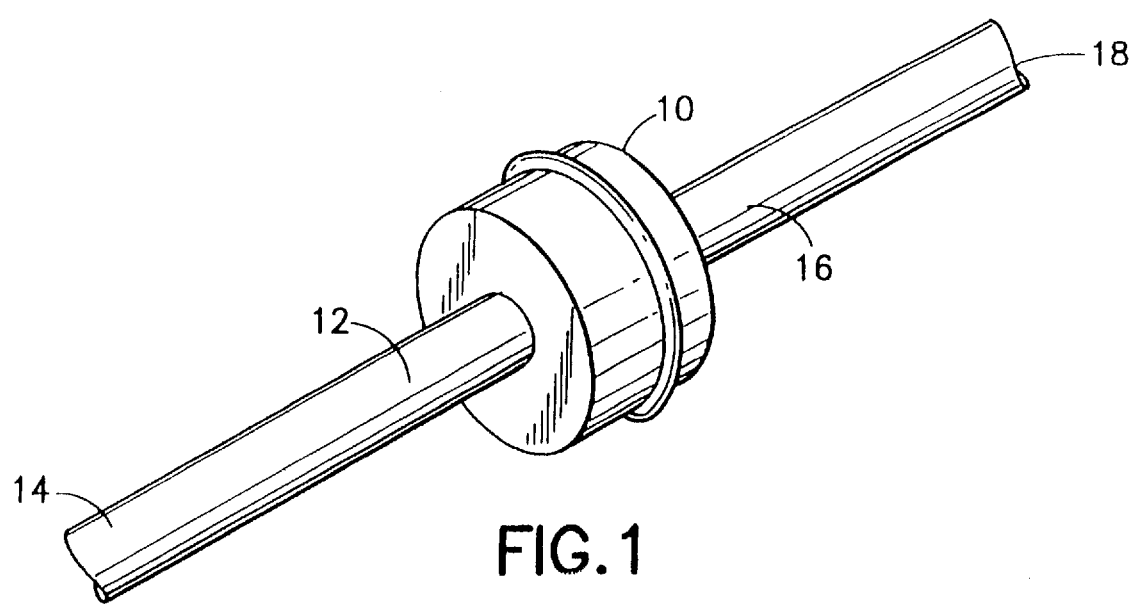
FIG. 1 is a flow restricting orifice such as may be usefully employed in the broad practice of the invention, to limit the flow of impurity-containing gas to a piezoelectric crystal sensor of the invention.

The present invention utilizes piezoelectric crystals coated with electrode sensor materials such as thin metal film coatings of Cu, Zn, Ag, Al, Cr, etc., to provide highly sensitive detectors for halide and other gases, when the gases contact and react with the electrode sensor material under operating conditions.

In the sensor of the invention, the piezoelectric crystal coated with the electrode sensor material is subjected to an input frequency, such as by means of an appropriately constructed and arranged oscillator circuit coupled in operative relationship to the piezoelectric crystal. The output frequency of the piezoelectric crystal coated with the electrode sensor material then is monitored and the change of the frequency in relation to the natural harmonic frequency of the coated crystal is determined, e.g., by a cascaded counter assembly.

By this arrangement, the contacting of a halide gas with the coating material on the crystal will cause a reaction to yield a metal halide reaction product of different mass than the intial mass of the metal on the crystal. As a result of such mass change, the frequency response characteristics of the coated crystal will change, and this frequency change thus will reflect the presence of the halide component in the gas contacted with the coating film on the piezoelectric crystal.

Accordingly, in the practice of the invention involving sensing of halide gaseous components, the frequency of an oscillator in the piezoelectric crystal circuit thus may be readily monitored to detect halogenation of the electrode, involving chemical reactions such as the following:

$Zn + 2HCl = ZnCl_2 + H_2$ $Zn + F_2 = ZnF_2$

It is readily feasible in the practice of the invention to tailor the reactivity of the coating material on the piezoelectric crystal, by choice of different materials, to obtain the appropriate desired sensitivity to different trace gases. For example, set out below are several illustrative thermodynamic equilibrium constants, for the reaction of HCl with different electrode (piezoelectric crystal coating) materials:

$2HCl(g) + 2Ag = 2AgCl + H_2(g)$  Keq=$10^6$ $2HCl(g) + 2Cu = CuCl + H_2(g)$  Keq=$10^{17}$ $2HCl(g) + Zn = ZnCl_2 + H_2(g)$  Keq=$10^{35}$

From this list one would predict that of these three piezoelectric crystal coating materials, Zn would be the most sensitive to HCl, and Ag would be the least. In like manner, a desired sensitivity coating material can readily be selected, for various other and specific gas components of interest, in a given sensing or monitoring application of the present invention.

In the broad scope of practice of the present invention, the piezoelectric crystal features a coating of a material which is interactive with the gas species of interest, to yield an interaction product which alters the frequency response of the piezoelectric crystal, so that the presence of the gas species is readily detectable in the gas contacted with the coated crystal.

Thus, the coating material may suitably comprise a material which is irreversibly chemically reactive with the gas species of interest, to produce a reaction product which is of a different mass than the original coating material, being either greater or smaller in magnitude in relation to the virgin coating on the crystal.

Another issue which is important in the environmental fluid monitoring applications of the invention is keeping particulates away from the sensor element, in order to avoid false alarms due to additional loading of the particulates on the crystal.

To maintain such a constant flow and to avoid contamination of the sensor element with particulates, a frit or a flow restrictor may be deployed in the gas flow passage, e.g, conduit, through which the fluid from the environment being sampled is flowed for analysis. Such flow restriction means may be employed to force the flow to be purely or substantially diffusional in character, and it will act as a particle filter at the same time. An example of such a flow restrictor device 10 is shown in FIG. 1, interposed between conduit 12, whose end 14 is joined to the sensor housing (not shown) and conduit 16, whose end 18 is joined to a suitable inlet for intake of environmental fluid (also not shown).

The flow restrictor may in a specific embodiment comprise a ¼" teflon plug in a KF25 tee which has a single 5/16"-18 tapped hole in it to allow diffusion of the gas to the sensor. The single hole will provide enough medium for gas to diffuse through without clogging.

If there are many particulates in the fluid environment being monitored, then in place of such a single hole flow restrictor, a porous frit may alternatively be utilized.

In some instances, the gas being monitored for the presence of a specific halide may contain other halide species, or more generally, the coating material used in the sensor may be chemically reactive with a number of species in the gas. In such instances, it may be necessary to provide ancillary treatment of the gas to remove the species thereof which are not of interest in the monitoring or detection process.

For example, if the sensor is not selective for chloride gas of a specific type, but rather responds similiarly to all three chloride gases in a gas containing $BCl_3$, HCl, and $Cl_2$ in the fluid environment being monitored, then it may be desirable to install a guard column or other extraneous chloride gas removal means, upstream of the sensor receiving the gas being monitored.

Thus, a reactive chemical removal agent for use in a guard column can be selected by examination of standard electrode potentials. For example, in the case of a two-component gas mixture (HCl and $Cl_2$) where the sensor is intended to selectively detect HCl but not $Cl_2$, electrode potential analysis shows that Fe(II) may be usefully employed in a guard column to obtain this selectivity. A positive net electrode potential (E) yields a favorable reaction, and a negative E yields an unfavorable reaction, in respect of the following reactions: $Fe(II)+Cl_2 \rightarrow Fe(III)+2Cl^-$ E=0.589V (favorable)

$FeCl_2+HCl \rightarrow FeCl_3+\frac{1}{2}H_2$ E=−0.771V (unfavorable)

Cu or Cu(I) would also be sufficient for this purpose, as shown by the following reactions:

$Cu+Cl_2 \rightarrow Cu(I)+2Cl^-$ E=0.84V (favorable)

$Cu(I)+Cl_2 \rightarrow Cu(II)+2Cl^-$ E=1.207V (favorable)

$Cu+HCl \rightarrow CuCl_2+H_2$ E=−0.52V (unfavorable)

$CuCl+HCl \rightarrow CuCl_2+H_2$ E=−0.153V (unfavorable)

Pb or Ca would not be suitable candidate materials for such purpose because they both react favorably with HCl and $Cl_2$.

To determine the proper species of removal agent for the guard column one must examine the standard electrode potentials of the components. If the addition of the electrode potentials for the two components is positive then the reaction is favorable, and if the addition is negative then the reaction will not occur readily. There are many possible choices for materials which will selectively react with the gas component to be masked from exposure to the sensor. Care must be exercised in this determination to pick a reactive component which reacts only with the gas species to be masked, and not the gas species to be sensed by the piezoelectric sensor.

Modification of the sensor coatings to provide oxidizing characteristics may be utilized as a suitable technique to provide sensitivity to hydride gases. For example, oxidation of a Cu, Cr, or Ag electrode coating to the corresponding oxide salt may be carried out for such purpose. Such oxides react with the hydrides to form non-volatile salts (and hydrogen/water). There is a net gain in weight (relative to the starting sensor coating material) when such reaction occurs. Mass-sensitive piezoelectric sensors can thus be used to readily and economically detect the occurrence of such reaction:

$3CuO+2AsH_3 \rightarrow Cu_3As_2+3H_2O$

As in the case of the chloride reactions, it is possible within the broad scope of the invention to readily tailor the reactivity of the sensor material and guard bed reactive material for a specific end use application of the present invention.

The sensor device of the present invention may be readily fabricated and deployed to provide accurate and reliable sensing of impurity species of interest in a wide variety of fluid environments, e.g., air or other ambient gases.

Point of use envimomental sensors according to the present invention may utilize a simple pump arrangement to draw ambient gases across the face of the sensor, with the sensed change in frequency being used to determine the concentration of the impurity gas species in the ambient environment. The output of such environmental sensor can be time averaged or instantaneous in character.

Sampling of gas from the environment being monitored may be effected by flowing the gas sampled from the environment through a tube at a suitably low flow rate, with the sensor being disposed in the tube and mounted for sensing of the gas. Such an arrangement does not require additional dilution flow and can operate in a low flow regime.

Figure 2:
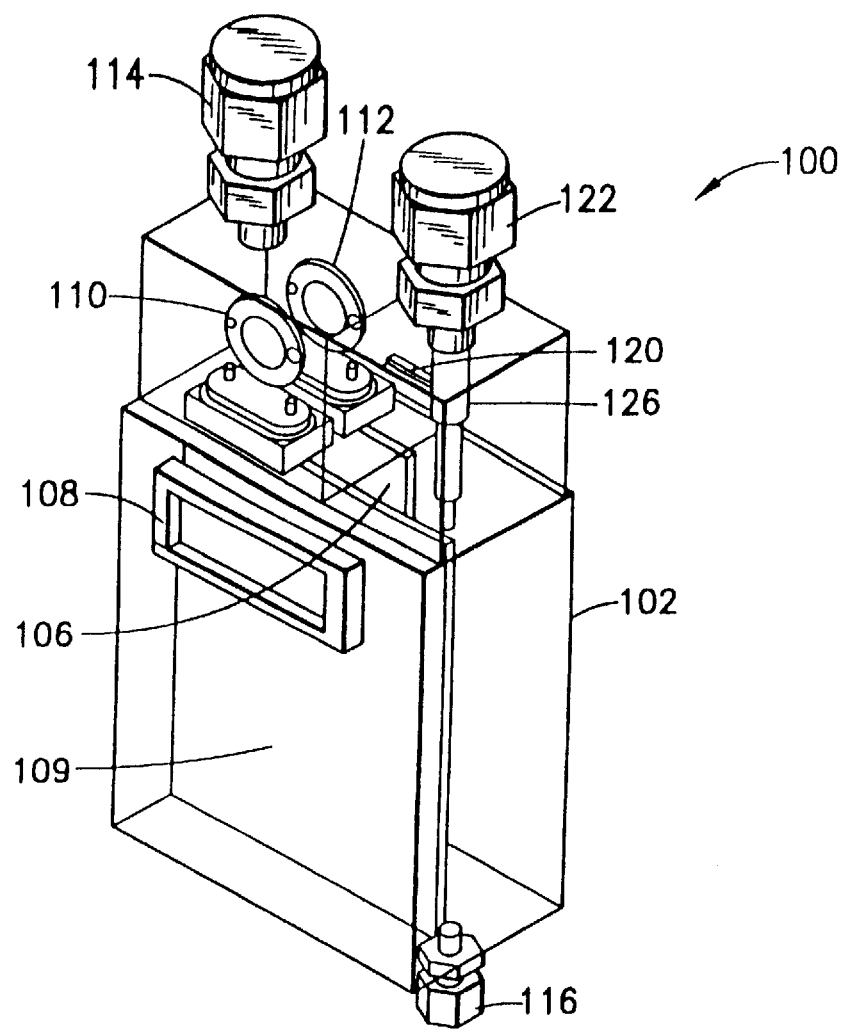
FIG. 2 is a perspective schematic view of an environmental fluid monitor assembly according to one embodiment of the invention.

An environmental monitoring assembly according to one embodiment of the invention is shown in FIG. 2. This environmental monitoring assembly 100 comprises a housing 102 containing therein a microelectronics module comprising motherboard 104 and ancillary board 106 which are operatively interconnected to the gas sensor element 112. The gas sensor element comprises a piezoelectric crystal having coated thereon a thin film of a sensor material with which the specific gas of interest is reactive to yield a metal-containing reaction product, as well as to the moisture sensor element 110 comprising a piezoelectric crystal. The moisture sensor element 110 may comprise an uncoated piezoelectric crystal, or it may have coated thereon a thin film of a sensor material 111 with which the water in the sampled gas is reactive to yield a metal hydride and/or metal oxide reaction product.

Alternatively, another type of moisture sensor element or assembly could be used, such as capacitive hygrometers, resistive hygrometers, etc.

The microelectronics module is in turn operatively connected to the output means comprising liquid crystal display 108 which may numerically display a concentration value for the gas species being monitored. Alternatively or additionally, the output means may provide a colorimetric display, e.g., with red indicating a hazardous or dangerously high concentration of the gas component of interest, yellow indicating a tolerable but high concentration of the gas component, and green indicating that the gas component concentration is within acceptable concentration limits. As still other alternatives, the output means may comprise a audible alarm, other visual diplay (e.g., a flashing light), a tactile indicating means such as a vibratory oscillator when the monitoring unit is worn on the person of a user thereof, or any other suitable output means.

The factors which control the response of the environmental monitor of FIG. 2 are flow rate (FR), the concentration of water, the monitored gas species concentration, and the life of the piezoelectric crystal. The response is not linear over the life of the crystal.

In the environmental monitor of FIG. 2, the sample gas is pulled across the two sensor elements 110 and 112 by an eductor 126. Gas is supplied to the eductor by eductor gas inlet 116, which may be suitably coupled to a source of driver gas, such as a container of compressed air. The eductor features suction tube 120 for drawing air, admitted into the housing by inlet fitting 114, across the sensor elements to the gas outlet 122. A frit (not shown) is provided in the inlet fitting 114 to the sensor cavity, to prevent particulate contamination. There is a second flow limiting orifice or frit (also not shown) in the inlet line to the eductor. This flow restriction provides constant flow through the sensor chamber. This constant flow condition can be maintained if the pressure on the low pressure side of the flow restriction is less than ½ the pressure on the upstream side of the flow restriction.

The concentration of water is measured by the piezoelectric crystal sensor 110. Alternatively, other moisture sensor means may be employed as discussed hereinabove.

Figure 3:
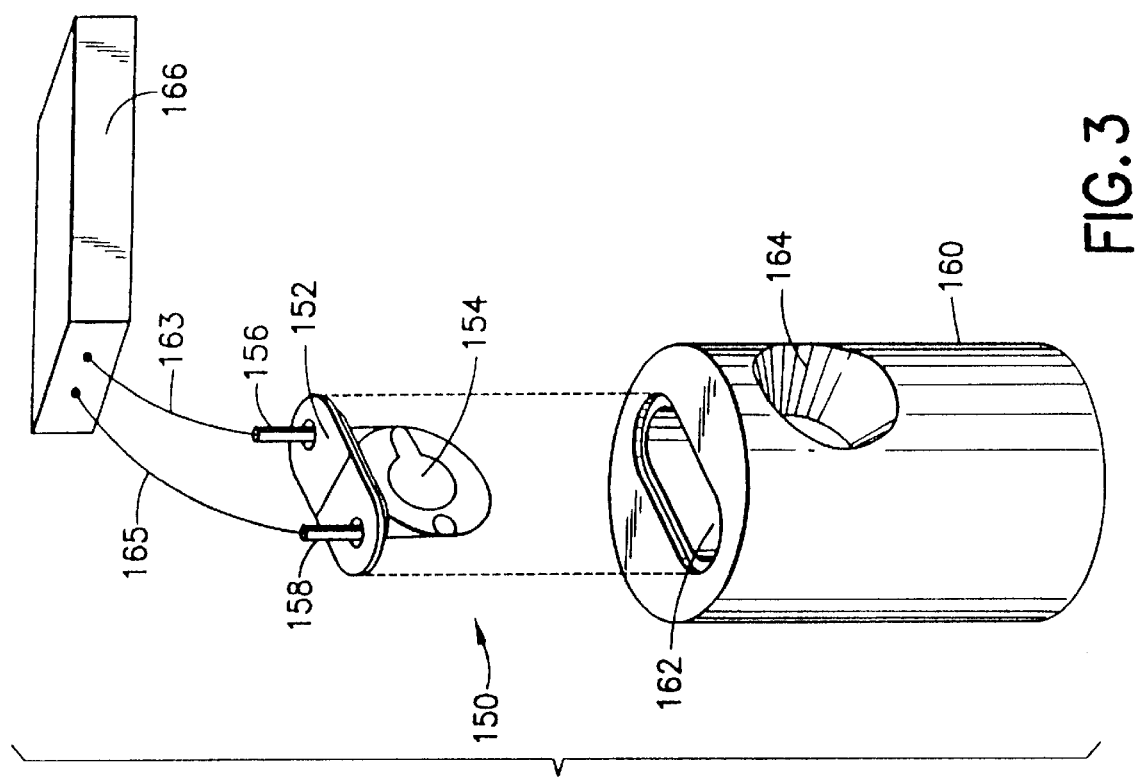
FIG. 3 is a sensor assembly, according to another embodiment of the invention.

FIG. 3 shows an exploded view of a sensor assembly according to another embodiment of the invention, comprising the sensor element 150 and the housing 160. The sensor element 150 comprises the piezoelectric crystal 154 which is coated with a suitable material interacting with the fluid component of interest to yield an interaction product of differing mass characteristic than the original coating material. The coated crystal is mounted on the plug member 152, with the respective leads of the piezoelectric crystal 154 protruding exteriorly of the plug member when the plug member is engaged with the housing 160 with the coated crystal extending into the cavity 162.

The housing 160 features an opening 164 by which a gas can be flowed into the cavity 162 containing the sensor element 150. Although not shown in the front perspective view of FIG. 3, the housing 160 has another opening therein, opposite opening 164 and in register with such opening, for discharge from the housing of the gas flowed past the coated piezoelectric crystal.

The leads 156 and 158 of the sensor element may be coupled in circuit relationship to suitable electronics means shown schematically as electronics module 166 in FIG. 3, by which the presence and concentration of the gas impurity species can be detected. The electronics module 166 is coupled to the sensor element leads 156 and 158 by wires 163 and 165, respectively.

Electronics module 166 provides the functions of (i) sampling the output resonant frequency of the piezoelectric crystal while the oscillating electric field is applied thereto, (ii) determining the change in resonant frequency from the fundamental resonant frequency incident to the formation of the solid interaction product when the sensor material interacts with the trace fluid component of interest in the fluid being monitored, and (iii) generating an output indicative of the presence of the trace fluid component in such fluid.

In a specific embodiment of the sensor assembly shown in FIG. 3, the housing 160 may comprise an aluminum housing which has the cavity 162 machined into it for insertion of the sensor element, as well as two feedthrough (¼" NPT) openings (opening 162 and the opposite opening not shown in FIG. 3) for the gas to flow through the sensor. In the body of this housing is the flow restricting orifice. This ¼" aluminum housing fits into the environmental fluid monitor's housing, and the front end driver electronics are plugged directly onto the legs (leads 156 and 158) of the sensor assembly.

Figure 4:
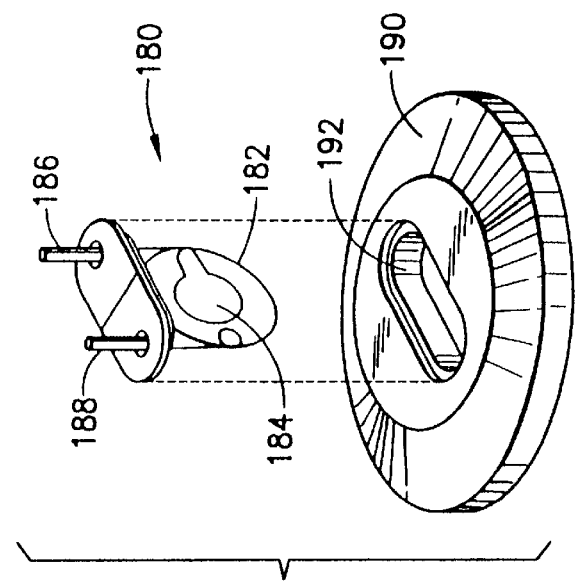
FIG. 4 is a sensor assembly, according to still another embodiment of the invention.

FIG. 4 is an exploded perspective view of another sensor assembly according to the present invention, comprising the sensor element 180 and the receiving fitting 190. The sensor element 180 comprises the piezoelectric crystal 182 which is coated with a suitable material interacting with the fluid component of interest to yield an interaction product of differing mass characteristic than the original coating material. The coated crystal is mounted on the plug member 184, with the respective leads 186 and 188 of the piezoelectric crystal protruding exteriorly of the plug member when the plug member is engaged with the receiving fitting 190 with the coated crystal extending into the cavity 192.

In a specific embodiment, the receiving fitting comprises a KF25 blank which will fit into a KF25 tee having a flow restricting orifice in the same leg as the sensor. The electronics associated with the sensor element plug directly into the legs of the sensor unit (leads 186 and 188).

It will be appreciated that the sensor device of the invention may assume a wide variety of conformations and arrangements in the broad practice of the invention, consistent with the specific end use fluid environment of the sensor device, and the nature and extent of the output function thereof.

Figure 5:
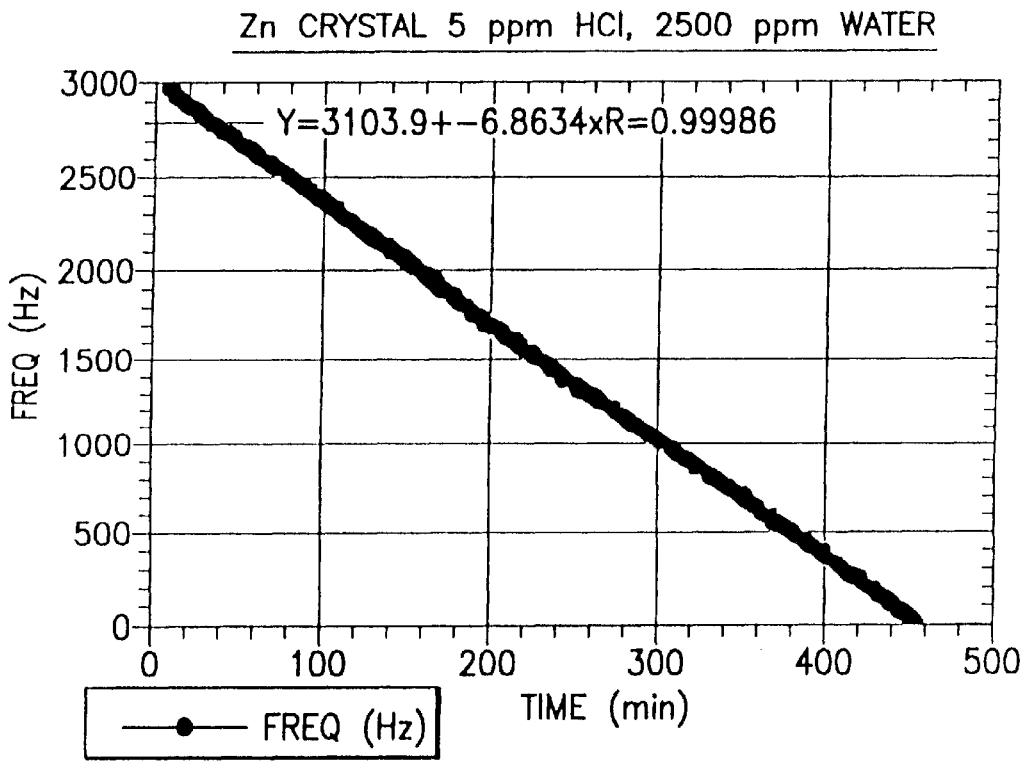
FIG. 5 is a graph of frequency response as a function of time, for a Zn electrode piezoelectric crystal sensor, in exposure to HCl at 5 ppm concentration and 2500 ppm water.

FIG. 5 is a graph of frequency as a function of time, showing the frequency response of a Zn electrode piezoelectric crystal sensor according to an illustrative embodiment of the invention, in exposure to HCl. The slope of the line in this plot determines the frequency change expected over time at 5 ppm HCl, 2500 ppm water, and 50 sccm HCl. This number is 6.9 Hz/min. To put this number in perspective, if sampling were carried out for 10 min. the expected frequency change would be 70 Hz, and the signal to noise (S/N) ratio is 35. Such frequency change is easily detected with the system of the present invention.

Figure 6:
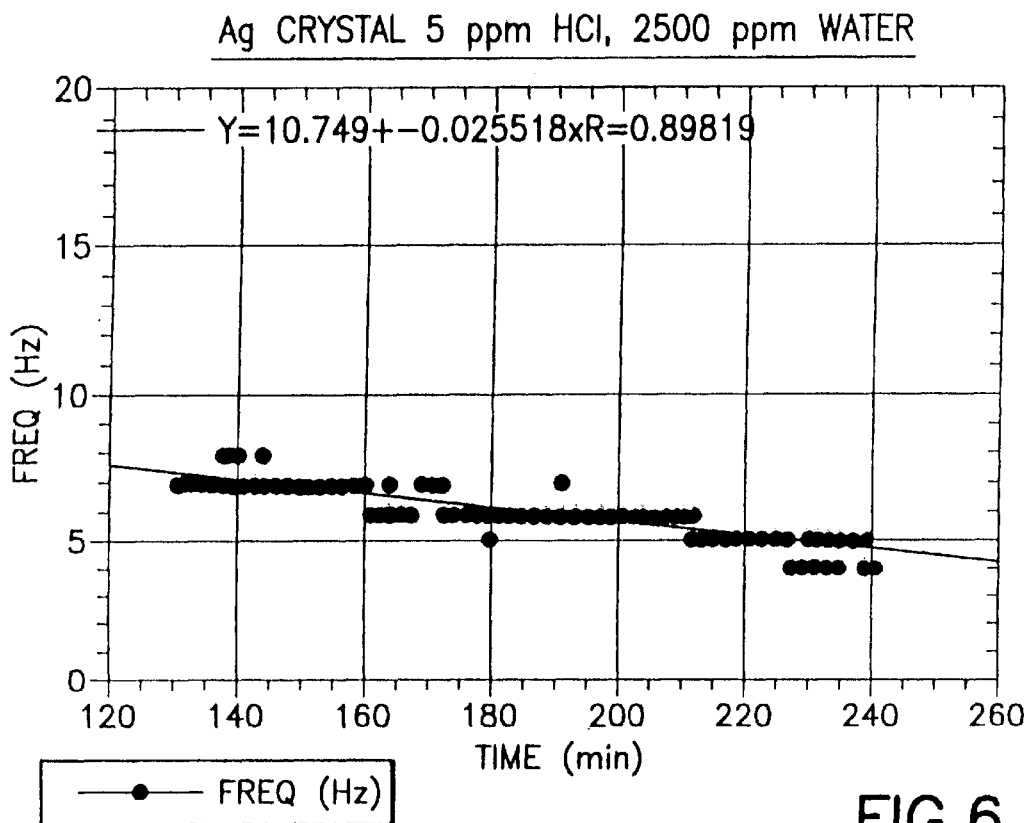
FIG. 6 is a graph of of frequency response as a function of time, for a Ag piezoelectric crystal electrode sensor, in response to HCl at 5 ppm concentration and 2500 ppm water.

FIG. 6 is a graph of frequency as a function of time, showing the frequency response of a silver (Ag) electrode piezoelectric crystal sensor according to an illustrative embodiment of the invention, in exposure to HCl. The frequency response over this interval, 0.025 Hz/min, is much smaller than that obtained with the Zn electrode (see FIG. 5), and corresponds to a 0.2 Hz change at a ten minute sampling period. In general, the Ag electrode sensor is much less sensitive than the zinc electrode, as predicted hereinabove.

Figure 7:
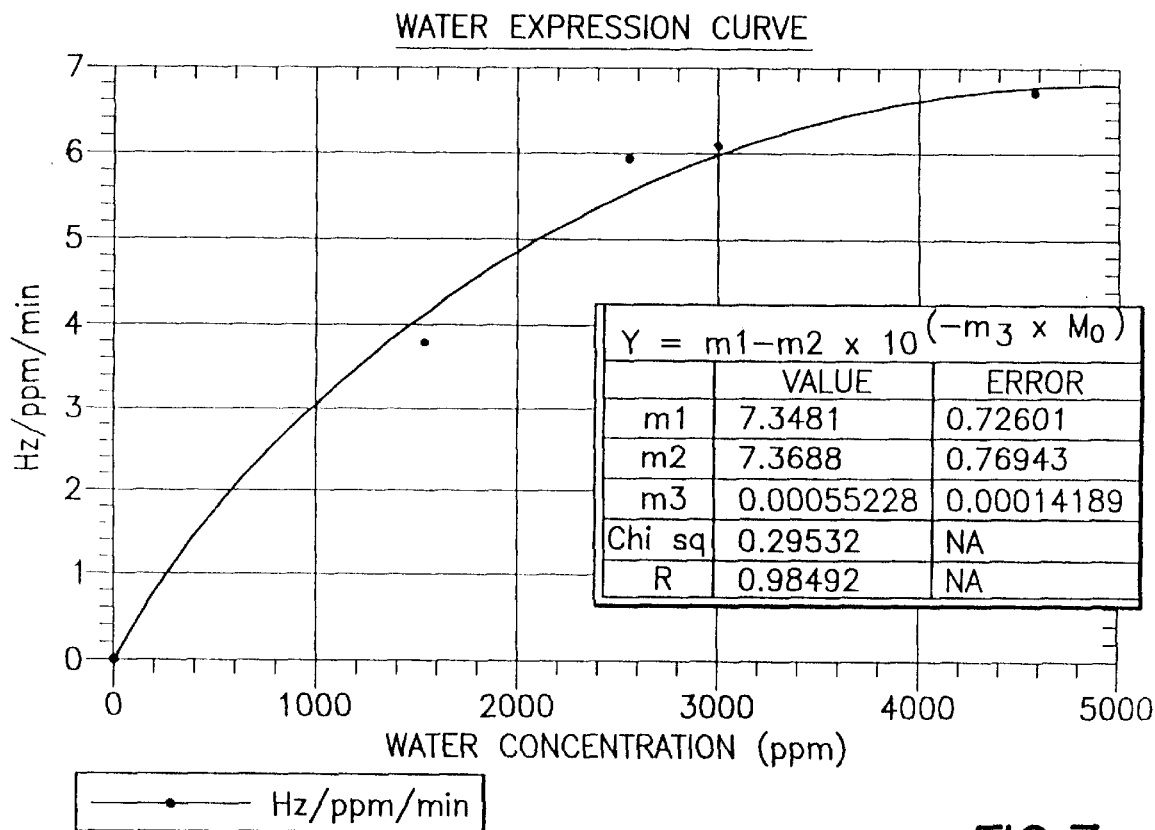
FIG. 7 is a graph of frequency as a function of water concentration, in ppm, showing the frequency response of a zinc electrode piezoelectric crystal sensor, determined with $BCl_3$.

FIG. 7 is a graph of frequency as a function of water concentration, in ppm, showing the frequency response of a zinc electrode piezoelectric crystal sensor according to an illustrative embodiment of the invention. The effect of water on the zinc sensor coating was determined by examining the frequency change over time with variation in water concentration, and with the water dependance curve determined with $BCl_3$. This figure shows that water is a catalyst in the corrosion reaction and that it accelerates the reaction to a point. At a maximum water concentration the rate of the reaction is constant. The water concentration at which the rate is constant is approximately 3000 ppm.

Figure 8:
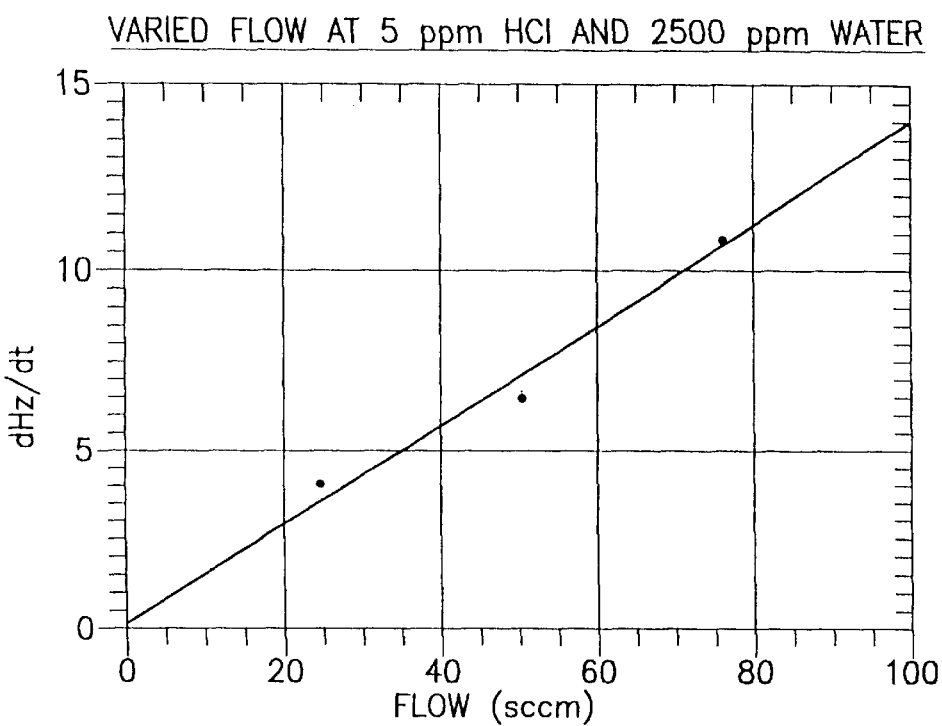
FIG. 8 is a graph showing a zinc electrode coated piezoelectric crystal sensor frequency response as a function of flow in standard cubic feet of gas per minute (sccm), with varied flow at 5 ppm HCl and 2500 ppm water.

The graph of FIG. 8 shows zinc electrode coated piezoelectric crystal sensor frequency response as a finction of flow in standard cubic feet of gas per minute (sccm), with varied flow at 5 ppm HCl and 2500 ppm water. From this data it is seen that as the flow doubles the frequency response rate of change, dHz/dt, doubles as well, indicative of a first order dependance relationship.

Figure 9:
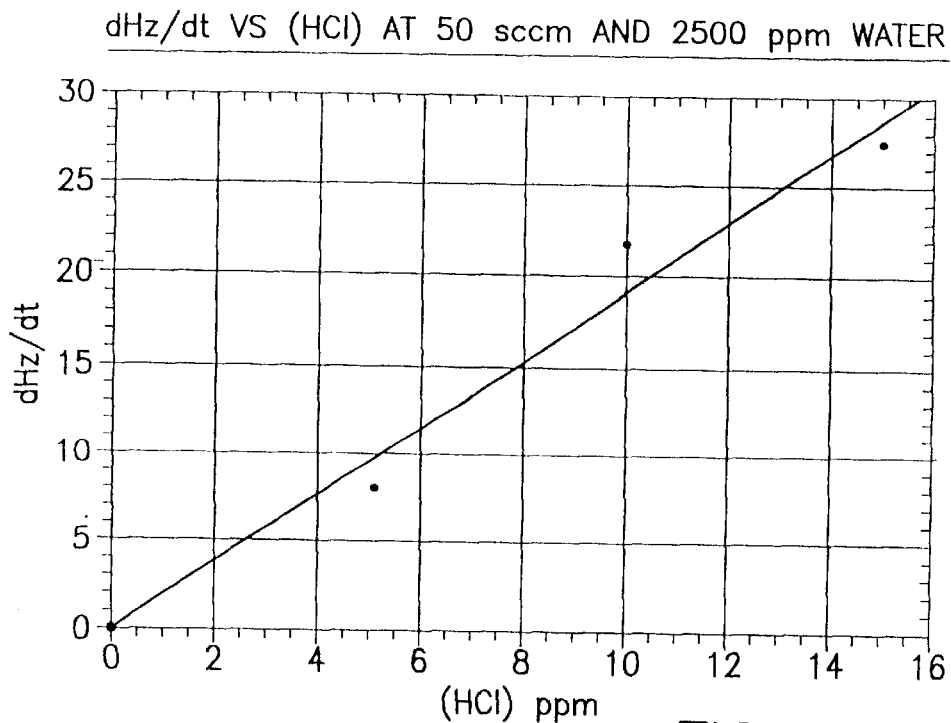
FIG. 9 is a graph of dHz/dt, the rate of frequency change, as a function of chloride concentration, for a Zn electrode sensor device, at constant flow, temperature and pressure, at 50 sccm and 2500 ppm water conditions.

FIG. 9 is a graph of dHz/dt, the rate of frequency change, as a function of chloride concentration, for a Zn electrode sensor device. FIG. 9 shows this data (dHz/dt vs HCl concentration) at constant flow, temperature and pressure, at 50 sccm at 2500 ppm water conditions.

Figure 10:
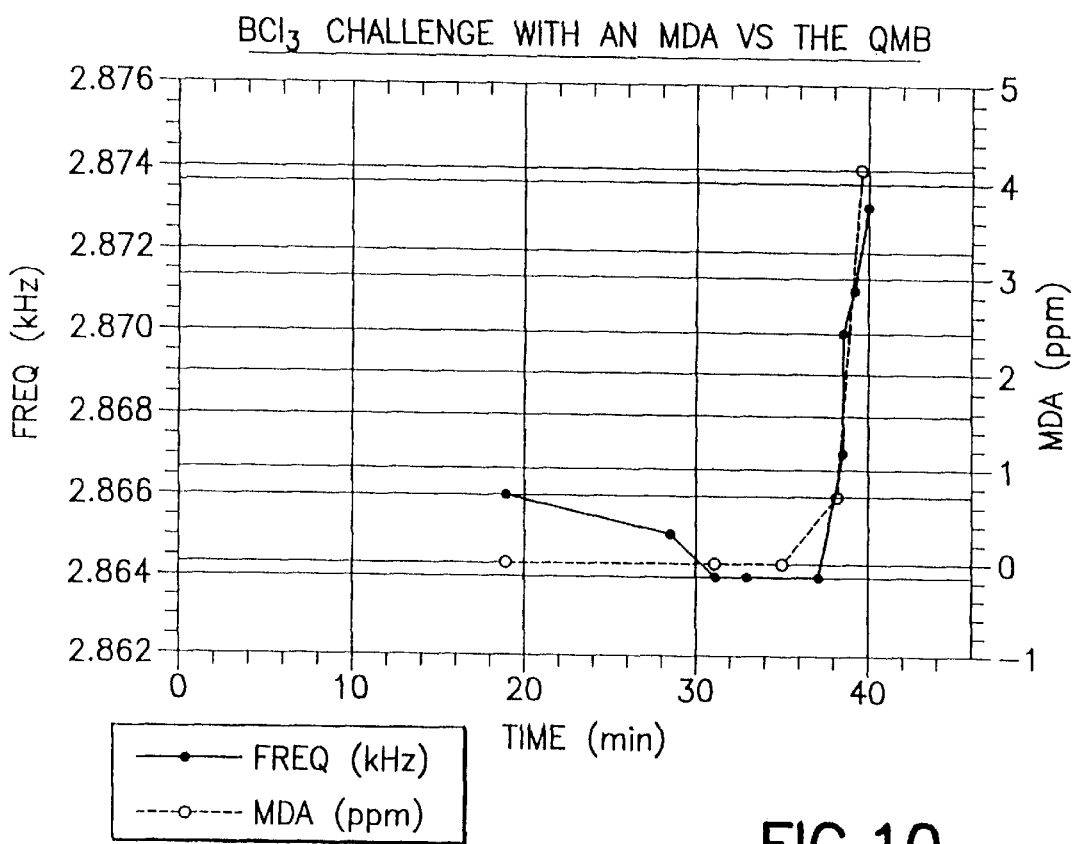
FIG. 10 is a graph of frequency as a function of time, showing the response characteristics of a sensor representative of the present invention, and the response characteristics of an MDA sensor, with boron trichloride ($BCl_3$).

FIG. 10 is a graph of frequency as a function of time, showing the response characteristics of a sensor representative of the present invention, and the response characteristics of an MDA sensor, with boron trichloride ($BCl_3$). The data show that the sensor of the present invention has similiar response times as the MDA sensor.

Figure 11:
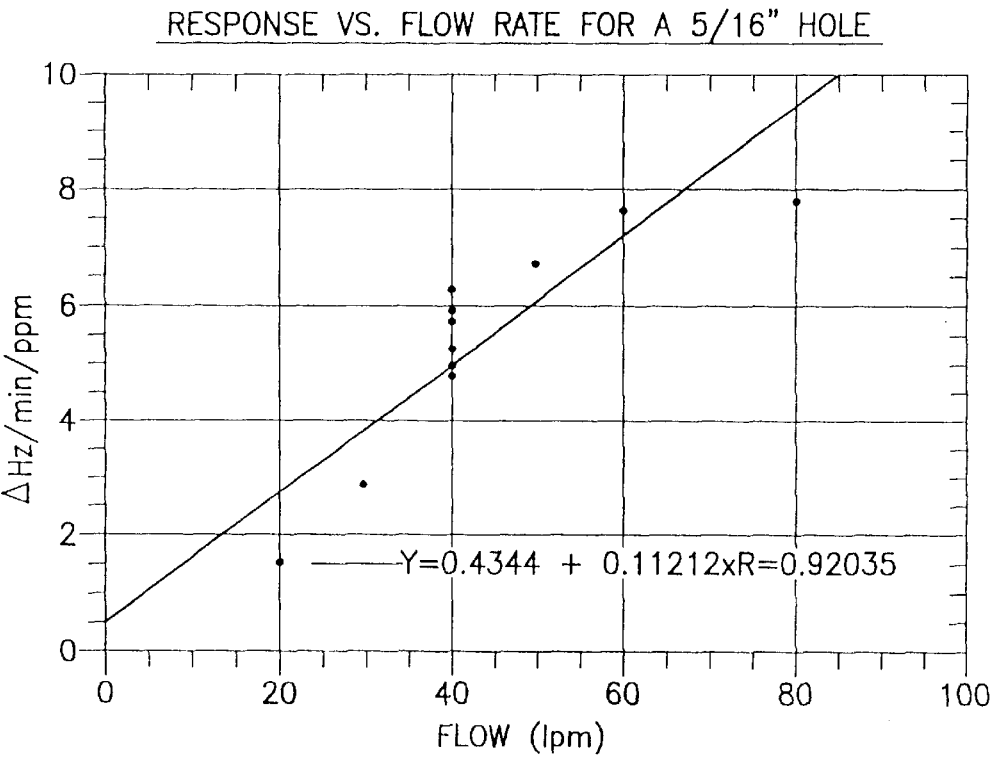
FIG. 11 is a graph of a flow rate frequency response curve for a Zn electrode piezoelectric crystal sensor utilizing a flow restricting orifice.

The response of the piezoelectric crystal sensor of the invention is proportional to the flow rate. FIG. 11 is a graph of the frequency response (change of frequency per unit time per ppm of HCl), as a function of flow rate of gas in liters per minute (1 pm). This graph shows the frequency response of a Zn electrode piezoelectric crystal sensor to HCl at different flow rates when utilizing a flow restricting orifice with an inside diameter of 5/16 inch.

Figure 12:
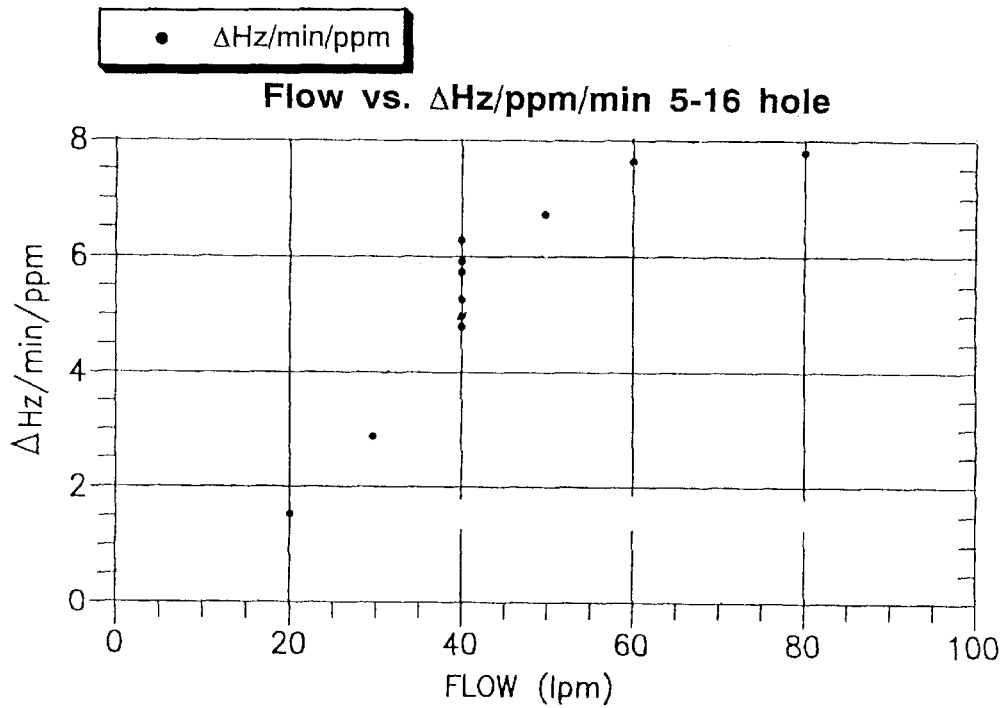
FIG. 12 is a graph of the rate of change of frequency per unit of trace impurity, as a function of the flow rate of the fluid stream containing such impurity, for a Zn electrode piezoelectric sensor according to one embodiment of the invention, in which a 5/16 inch flow restricting orifice is employed to restrict the flow of the impurity (HCl)-containing fluid to the sensor.

FIG. 12 is a graph of the rate of change of frequency per unit of trace impurity, as a function of the flow rate of the fluid stream containing such impurity, for a Zn electrode piezoelectric sensor, in which a 5/16 inch flow restricting orifice is employed to restrict the flow of the impurity (HCl)-containing fluid to the sensor. As shown by this graph, the flow restriction afforded by the orifice is sufficient to accomodate a 40 liter per minute flow of HCl-containing gas, restricting the flux at the Zn coating on the piezoelectric crystal so that the Δfrequency/minute/ppm of HCl is in the range of 4.8 to 6.4, thereby providing excellent dynamic frequency response characteristics consistent with superior operating life of the sensor.

Various of the foregoing graphs and examples reflect flow rates of significant magnitude, above the magnitude of rates which may be employed in most environmental fluid monitoring applications. Nonetheless, these examples, variously reflecting the use of flow restriction means to attenuate the flux of the reactive fluid species on the piezoelectric crystal coating, are useful in illustrating the operational characteristics of coated piezoelectric crystals which are usefully employed in environmental fluid monitor apparatus and processes within the broad scope of the instant invention.

Thus, the foregoing data and examples show that the piezoelectric crystal sensor of the invention provides an effective and simple means and method for determining the presence of a dilute or trace component in a fluid. The invention contemplates the provision on a piezoelectric crystal substrate of a reactive coating which posesses high sensitivity and selectivity for a wide variety of gas species, e.g., chlorides, fluorides, hydrides, etc. in correspondingly diverse fluid environments.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. An environmental gas monitor for detection of a trace fluid in a fluid environment, comprising:

a piezoelectric crystal having a fundamental resonant frequency in response to an applied oscillating electric field;

a coating on the piezoelectric crystal of a sensor material which is reactive with the trace fluid component to yield a solid interaction product of changed mass in relation to the initial mass of the sensor material interacting with the trace fluid component to yield the solid interaction product;

means for applying an oscillating electric field to the piezoelectric crystal which generates an output resonant frequency therefrom;

means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the trace fluid component in the environment; and a flow control means for controllably flowing a selected flow rate of fluid from said fluid environment in contact with the sensor material on said piezoelectric crystal, and wherein the means for performing finctions (i), (ii) and (iii), comprise computational means for determining, based on said output indicative of the presence of the trace fluid component in said environment, a calculated concentration of said trace fluid component in said fluid environment, in accordance with the algorithm:

$$dF/dt = d \cdot [C_i] \cdot Q$$

wherein:

dF/dt is the time-variant differential rate of change of frequency from the fundamental resonant frequency of the piezoelectric crystal coated with the sensor material as sampled by said means for performing function (i), (ii) and (iii);

d is a proportionality constant;

$[C_i]$ is the concentration of the trace fluid component;

Q is the volumetric flow rate of the fluid of the fluid environment; and the coated piezoelectric crystal exhibits a frequency response rate to the trace fluid component in the range of about 0.001 to about 1000 Hertz/min/(part-per-million of the fluid component).

2. An environmental gas monitor according to claim 1, wherein the piezoelectric crystal comprises a piezoelectric silica crystal.

3. An environmental gas monitor according to claim 1, wherein the coating of sensor material comprises a chemisorbent material which is chemically reactive with the trace fluid component.

4. An environmental gas monitor according to claim 1, wherein the piezoelectric crystal has a fundamental resonant frequency in the range of from 1 megahertz to 10 megahertz.

5. An environmental gas monitor according to claim 1, wherein the means for (i) sampling the output resonant frequency of the piezoelectric crystal while said oscillating electric field is applied thereto, (ii) determining the change in resonant frequency from the fundamental resonant frequency incident to the formation of said solid interaction product when the sensor material interacts with said trace fluid component in said fluid environment, and (iii) generating an output indicative of the presence of the trace fluid component in said environment, comprises a circuit including therein a cascaded array of frequency counters.

6. An environmental gas monitor according to claim 1, further comprising an eductor including an eductor suction tube for drawing fluid from the fluid environment along a flow path for contacting thereof with the sensor material, and gas inlet and gas outlet passages for applying suction to the eductor suction tube.

7. An environmental gas monitor according to claim 1, wherein the sensor material comprises a thin film metal.

8. A sensor according to claim 7, wherein the thin film metal is selected from the group consisting of copper, zinc, silver, aluminum and chromium.

9. An environmental gas monitor according to claim 1, further comprising a second sensor for sensing the presence of water vapor in the fluid environment.

10. An environmental gas monitor according to claim 9, further comprising means for determining concentration of trace fluid component in the fluid environment, and for utilizing the sensing of the presence of water vapor in the fluid environment to adjust concentration determined for the trace fluid component, for water vapor in the fluid environment.

11. An environmental gas monitor according to claim 1, wherein the coated piezoelectric crystal exhibits a frequency response rate to the trace fluid component in the range of from about 0.1 to about 50 Hertz/min/(part-per-million of the fluid component).

12. An environmental gas monitor according to claim 1, wherein the coated piezoelectric crystal exhibits a frequency response rate to the trace fluid component in the range of from about 0.5 to about 10 Hertz/min/(part-per-million of the fluid component).

13. An environmental gas monitor according to claim 1, wherein the means for flowing fluid from the fluid environment at a constant flow rate to the coating on the piezoelectric crystal comprise a flow passage containing a flow limiting structure therein, characterized by a pressure on a low pressure side of the flow limiting structure being less than ½ the pressure on an upstream side of the flow limiting structure.

14. An environmental gas monitor according to claim 1, wherein the flow control means is constructed and arranged to prevent particulate solids in the fluid environment from contacting the sensor material.

15. An environmental monitoring assembly comprising a housing containing therein (i) a gas sensor assembly including (A) a piezoelectric crystal having coated thereon a thin film of a sensor material with which a specific environmental gas species is reactive to yield a metal-containing reaction product, and (B) a moisture sensor, (ii) an electronics module operatively connected to the gas assembly, and arranged to determine the presence of the specific environmental gas species as sensed by the gas sensing assembly, (iii) output means operatively coupled with the electronics module and arranged for displaying an output indicative of the presence of the specific environmental gas species as sensed by the gas sensing assembly, and (iv) means for drawing fluid from the fluid environment in contact with the gas assembly at a constant flow rate so that the specific environmental gas species when present reacts with the sensor material to form the metal-containing reaction product;

wherein:
said means for drawing fluid from the fluid environment in contact with the gas sensing assembly at a constant flow rate comprises an eductor, and the coated piezoelectric crystal exhibits a frequency response rate to the trace fluid component in the range of from about 0.0001 to about 1000 Hertz/min/(part-per-million of the fluid component).

16. A method for detection of a trace fluid component in a fluid environment and calculating the concentration of same, comprising:

providing a piezoelectric crystal having a fundamental resonant frequency in response to an applied oscillating electric field with a coating on the piezoelectric crystal of a sensor material which is reactive with the trace fluid component to yield a solid interaction product of changed mass in relation to the initial mass of the sensor material interacting with the trace fluid component to yield the solid interaction product;

applying an oscillating electric field to the piezoelectric crystal which generates an output resonant frequency therefrom;

sampling the output resonant frequency of the piezoelectric crystal while the oscillating electric field is applied thereto;

determining the change in resonant frequency from the fundamental resonant frequency that occurs on formation of the solid interaction product when the sensor material interacts with the trace fluid component in the fluid environment;

generating an output indicative of the presence of the trace fluid component in the environment;

flowing fluid from the fluid environment at a constant flow rate to the coating on the piezoelectric crystal so that the trace fluid component when present reacts with the coating to form the solid interaction product; and using the output indicative of the presence of the trace fluid in said environment, calculating the concentration of said trace fluid in said environment in accordance with the algorithm:

$$dF/dt = d \cdot [C_i] Q$$

wherein:
dF/dt is the time-variant differential rate of change of frequency from the fundamental resonant frequency of the piezoelectric crystal coated with the sensor material as sampled as described by the above functions;

d is a proportionality constant;

$[C_i]$ is the concentration of the trace fluid component;

Q is the volumetric flow rate of the fluid of the fluid environment; and the piezoelectric crystal exhibits a frequency response rate to the trace fluid component in the range of from about 0.001 to about 1000 Hertz/min/(part-per-million of the fluid component).

17. A process according to claim 16, wherein the output indicative of the presence of the trace fluid component in the environment comprises a concentration of the trace fluid in the fluid environment.

18. A process according to claim 17, further comprising monitoring concentration of water vapor in said fluid environment, and correctively adjusting concentration of the trace fluid thereto.

* * * * *

UNITED STATES PATENT AND TRADEMARK OFFICE
CERTIFICATE OF CORRECTION

PATENT NO. : 5,817,921
DATED : October 6, 1998
INVENTOR(S) : G. Tom and C. Miller It is certified that error appears in the above-indentified patent and that said Letters Patent is hereby corrected as shown below:

Column 10, line 28, change "finction" to --function--
Column 11, line 51, change "finctions" to -- functions --

Column 14, line 20, change "$dF/dt=d \cdot [C_i]Q$" to -- $dF/dt=d \cdot [C_i] \cdot Q$ --

Signed and Sealed this

Twenty-third Day of February, 1999

Attest:

Q. TODD DICKINSON

*Attesting Officer*   *Acting Commissioner of Patents and Trademarks*